United States Patent
Sanchez Jimena et al.

(10) Patent No.: US 10,624,355 B2
(45) Date of Patent: Apr. 21, 2020

(54) MODERN PREFERMENT METHOD FOR MANUFACTURING DOUGH MIXTURE

(71) Applicant: LALLEMAND INC., Montreal, Quebec (CA)

(72) Inventors: Ana Sanchez Jimena, Blagnac (FR); J Kevin Kraus, Tenafly, NJ (US)

(73) Assignee: LALLEMAND, INC., Montreal, Quebec (CA)

( * ) Notice: Subject to any disclaimer, the term of this patent is extended or adjusted under 35 U.S.C. 154(b) by 494 days.

(21) Appl. No.: 14/912,181

(22) PCT Filed: Aug. 13, 2014

(86) PCT No.: PCT/CA2014/000617
§ 371 (c)(1),
(2) Date: Feb. 16, 2016

(87) PCT Pub. No.: WO2015/024097
PCT Pub. Date: Feb. 26, 2015

(65) Prior Publication Data
US 2016/0205952 A1 Jul. 21, 2016

Related U.S. Application Data

(60) Provisional application No. 61/867,761, filed on Aug. 20, 2013.

(51) Int. Cl.
- *A21D 8/04* (2006.01)
- *C12R 1/46* (2006.01)
- *A21D 6/00* (2006.01)

(52) U.S. Cl.
CPC ............. *A21D 8/045* (2013.01); *A21D 6/001* (2013.01); *A21D 8/047* (2013.01); *C12R 1/46* (2013.01)

(58) Field of Classification Search
None
See application file for complete search history.

(56) References Cited

U.S. PATENT DOCUMENTS

| | | |
|---|---|---|
| 3,404,984 A | 10/1968 | Olsen |
| 3,410,692 A | 11/1968 | Wutzel |
| 3,547,654 A * | 12/1970 | Olsen ............... A21D 8/045 426/20 |

(Continued)

FOREIGN PATENT DOCUMENTS

| | | |
|---|---|---|
| CA | 2726440 A1 | 12/2009 |
| EP | 0 093 635 A1 | 11/1983 |
| EP | 0 153 057 A2 | 8/1985 |
| JP | 2002-017240 A | 1/2002 |

(Continued)

OTHER PUBLICATIONS

Spivakova et al. RU 2228036 May 10, 2004 Derwent Abstract. (Year: 2004).*

(Continued)

*Primary Examiner* — Felicia C Turner
(74) *Attorney, Agent, or Firm* — Nutter McClennen & Fish LLP

(57) ABSTRACT

There is provided a lactic acid bacteria strain, *Lactococcus lactis* with accession number IDAC 270613-01, having a short fermentation lag phase of 1 to 5 hours which is compatible with modern bread making methods. Pre-ferment methods which use the strain for manufacture of leavened products and the leavened products produced therefrom are also disclosed.

11 Claims, 2 Drawing Sheets

(56) References Cited

U.S. PATENT DOCUMENTS

| | | | |
|---|---|---|---|
| 3,640,730 A * | 2/1972 | Rolland | A21D 2/00 426/253 |
| 4,243,687 A * | 1/1981 | Kline | C12N 1/04 426/62 |
| 5,185,165 A | 2/1993 | Lynn | |
| 5,221,617 A | 6/1993 | Lynn | |
| 5,316,776 A | 5/1994 | Annuk et al. | |
| 6,465,027 B1 | 10/2002 | Taillade et al. | |
| 2001/0051196 A1 | 12/2001 | Mutsaers | |
| 2003/0035860 A1 | 2/2003 | Ando et al. | |
| 2004/0166198 A1 * | 8/2004 | Kiers | A61K 36/00 426/49 |
| 2005/0053582 A1 | 3/2005 | Kringelum et al. | |
| 2005/0069862 A1 | 3/2005 | Kringelum et al. | |
| 2006/0204484 A1 | 9/2006 | Bisgaard-Frantzen et al. | |
| 2008/0131556 A1 | 6/2008 | De Simone et al. | |
| 2008/0152758 A1 * | 6/2008 | Zheng | A21D 2/24 426/9 |
| 2010/0310718 A1 | 12/2010 | Kringelum et al. | |

FOREIGN PATENT DOCUMENTS

| | | |
|---|---|---|
| JP | 2011-050365 A | 3/2011 |
| RU | 2228036 C2 | 5/2004 |

OTHER PUBLICATIONS

Banu, I., et al., "Quality Evaluation of the Sourdough Rye Breads," 2011, Annals U Dunarea De Jos Galati, V.35, pp. 94-105.

Extended European Search Report for Application No. EP 14838195.7, dated Jan. 4, 2017 (12 pages).

Gerekova, P. et al., "Importance of lactobacilli for bread-making industry," Acta Chimica Slovaca, vol. 4, pp. 118-135.

Kam, P. V., et al., "Inhibition of Mold Growth by Sourdough Bread Cultures," Rev. Undergrad. Res. Agricultural and Life Sciences (RURALS), V. 2, pp. 1-15.

Gaggiano, M. et al., "Defined multi-species, semi-liquid, ready-to-use sourdough starter," Food Microbiology, 2007, v. 24, pp. 15-24.

International Search Report and Written Opinion for Application No. PCT/CA2014/000617, dated Nov. 19, 2014 (11 pages).

* cited by examiner

MODERN PREFERMENT METHOD FOR MANUFACTURING DOUGH MIXTURE

CROSS REFERENCE TO RELATED APPLICATIONS

The present application is a '371 U.S. national phase application of PCT/CA2014/000617, filed Aug. 13, 2014, entitled "Modern Preferment Method for Manufacturing Dough Mixture," which claims priority to U.S. Provisional Application No. 61/867,761, filed Aug. 20, 2013, both applications of which are hereby incorporated by reference in their entirety.

FIELD OF THE INVENTION

The present invention relates to a modern preferment method. More particularly, the present invention relates to a modern preferment method of manufacturing a dough mixture and a dough mixture made therefrom.

BACKGROUND OF THE INVENTION

The preferment method, or sponge and dough method, is a two-step process in which a sponge is made and fermented for a given period of time (pre-fermentation), followed by the addition of the rest of the ingredients to the sponge. The pre-ferment or sponge generally consists of flour, water and a leavening agent.

Traditional bread making processes rely on long pre-fermentation times with yeast and bacteria to develop the dough texture and flavor. These pre-fermentation times also provide leavening and extend the mold-free shelf-life of the dough. In these traditional methods, bacteria starter cultures may be used to standardize the process and enhance the flavor. For instance, baker's yeast typically contains some lactic acid bacteria that are responsible for a mildly sour flavor in the bread, but the type and exact quantity of these bacteria may vary.

Conversely, modern bread making processes like the sponge and dough process use a shorter fermentation (or short preferment) with yeast alone to develop the dough texture, and flavor and provide leavening. Bacteria starter cultures are not used as their lag phase is generally not compatible with the short pre-ferment time. Since baker's yeast typically contains some lactic acid bacteria, such processes lack the standardization observed in traditional bread making methods.

The preferment provides the dough development, flavor and leavening. Yeast metabolizes the flour nutrients and produces yeast flavors (alcohol and esters for example) as well as $CO_2$. $CO_2$ dissolves in the dough in the form of carbonic acid ($H_2CO_3$) which in turn drives the dough pH from about 6.5-6 to about 5, the pH at which no more $CO_2$ is dissolved in the dough. The excess $CO_2$ is further degassed from the dough. Such a pH contributes to activating anti-molding organic acid-based preservatives (such as propionic, acetic and fumaric acids).

Consequently, breads or bread-like products produced using modern processes are more alcoholic and do not exhibit the characteristic flavor of traditional breads or bread-like products in which the long pre-fermentation time with yeast and bacteria results in a more complex and less alcoholic flavor.

Bacteria starter cultures are not used in the sponge since their lag phase is not compatible with the short preferment time. Lactic acid-producing bacteria (LAB) are, however, used along with wild yeasts in traditional methods with long pre-fermentation times for the production of sourdough. Sourdough breads and break-like products exhibit a mildly sour flavor due to the lactic acid and other organic acids produced and are characterized by an open and airy crumb texture.

Accordingly, there remains a need for improved modern processes of manufacturing a dough mixture that allow for the production of leavened products such as, for example, bread or bread-like products exhibiting a more complex flavor than modern processes currently used in the art with a dough quality, texture and leavening comparable to traditional processes.

SUMMARY OF THE INVENTION

In an aspect, there is provided a method for making a dough mixture, the method comprising the steps of a) mixing an effective amount of at least one lactic acid bacteria strain with a first portion of dough ingredients to form a preferment; b) allowing the preferment to ferment for 1 to 5 hours; and c) mixing the fermented preferment with the remaining portion of the dough ingredients to form the dough mixture.

In an aspect of the method, the at least one lactic acid bacteria strain has a short lag phase allowing the release of lactic acid during the fermentation until the pH becomes inhibitory to the growth of the at least one lactic acid bacteria strain. Accordingly, the acidity of the dough mixture is not characteristic of sourdough.

In another aspect of the method, the release of lactic acid from the at least one lactic acid bacteria strain decreases the pH of the preferment during the fermentation by at least 0.1 pH units more than the pH of a preferment that is fermented without the at least one lactic acid bacteria strain.

In an aspect of the method, the first portion of dough ingredients comprises flour, water and yeast.

In a further aspect of the method, the remaining portion of the dough ingredients comprises flour, water and yeast.

In a yet further aspect of the method, the first portion and the remaining portion of the dough ingredients comprises flour, water and yeast.

In an aspect of the method, the first portion and the remaining portion of the dough ingredients are free of yeast.

In another aspect of the method, the method further comprises the steps of cooling or freezing the fermented preferment obtained from step b) for a period up to 48 hours and warming the cooled or frozen fermented preferment before mixing with the remaining portion of the dough ingredients to form the dough mixture.

In another aspect, there is provided a fermented preferment obtainable at step b) of the method as defined above.

In a further aspect, there is also provided a dough mixture obtainable by the method as defined above.

In yet a further aspect there is provided a use of the dough mixture as defined above for the production of leavened products.

In an aspect of the method, in the preferment, in the dough mixture and in the use, the lactic acid bacteria strain is from the genera *Lactobacillus, Lactococcus, Streptococcus, Leuconostoc* or *Pediococcus*. In a further aspect of the method, in the preferment, in the dough mixture and in the use, the lactic acid bacteria strain is a *Lactococcus lactis* strain. In yet a further aspect of the method, in the preferment, in the dough mixture and in the use, the lactic acid bacteria strain is a biologically pure culture of *Lactococcus lactis*, strain R2207, having accession number IDAC 270613-01 filed on Jun. 27, 2013.

In still a further aspect, there is provided a biologically pure culture of *Lactococcus lactis*, strain R2207, having accession number IDAC 270613-01 filed on Jun. 27, 2013. Strain R2207 has been deposited by Lallemand Inc. 6100 Royalmount Ave, Montréal, Quebec, H4P 2R2, Canada.

DETAILED DESCRIPTION

Modern processes for making bread or bread-like products use short fermentation times with yeast alone (or short preferment) to develop the dough flavor, texture and leavening. Contrary to traditional bread making processes, modern bread making processes do not use bacteria starter cultures because their lag phase is generally not compatible with the shorter fermentation time of the processes.

The present description is based on the unexpected discovery that an effective amount of at least one lactic acid bacteria strain may be used in a short preferment method to produce a more complex flavored dough and leavened products produced therefrom. Depending on the process, the more complex flavored dough may also have a less alcoholic flavor. The more complex and less alcoholic flavored dough and leavened products produced therefrom are associated in the art with traditional processes, while modern processes used in the art with yeast only are associated with alcoholic and yeasty flavors.

Alternatively, an effective amount of at least one lactic acid bacteria may be used in traditional processes to shorten the pre-fermentation time.

Therefore, the present description provides lactic acid bacteria strains having a lag phase compatible with a modern leavened products making process, methods for manufacturing a dough mixture and leavened products made therefrom.

The term "leavened product" when used herein will be understood to refer to bread and bread-like products. Non-limiting example of bread-like products include rolls, bagels, wheat flour tortillas, pizza crusts, donuts, croissants and pita breads.

In an embodiment, there is provided a method for making a dough mixture. The method comprises a first step of mixing an effective amount of at least one lactic acid bacteria strain with a first portion of dough ingredients to form a preferment. In a second step, the preferment may be fermented. In a third step the fermented preferment obtained in the second step may be mixed with the remaining portion of the dough ingredients to form the dough mixture.

In one embodiment, the preferment is fermented for a period ranging between 1 to 5 hours, preferably between 2 to 4 hours. Such a method is defined as a short preferment.

The term "lactic acid bacteria strain" when used herein will be understood to refer to a lactic acid bacteria strain having a short lag phase allowing the quick release of lactic acid during the short preferment period until the pH becomes inhibitory to the growth of the at least one lactic acid bacteria strain.

Figure 1:
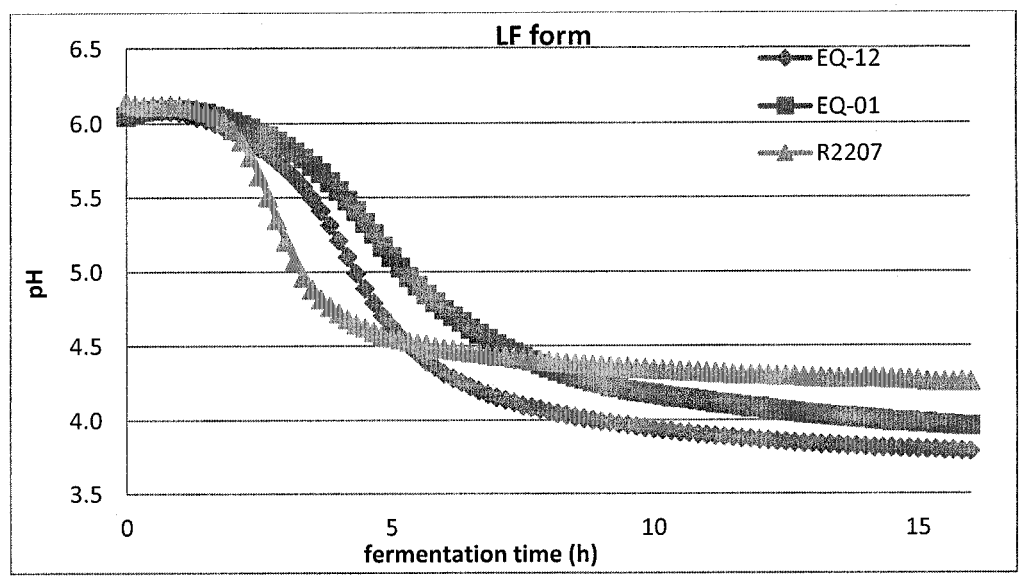
FIG. 1 illustrates the acidification activity of different lactic acid bacteria strains in liquid frozen form, showing the different lag phases characteristic from each strain in accordance with an embodiment of the invention.

The short lag phase of the at least one lactic acid bacteria strain of the present description may be characterized by a maximum rate of release of lactic acid during the first 4 hours of fermentation, preferably during the first 3 hours. As shown in FIG. 1, the at least one lactic acid bacteria strain also exhibits a limited acid tolerance characterized by a pH of at least 4.1 after 16 hours of fermentation and/or at least 4.3 after 12 hours of fermentation.

Contrary to the at least one lactic acid bacteria strain of the present description, "acid-tolerant" lactic acid bacteria strains do not exhibit a limited acid tolerance and are characterized by a pH below 4 after 16 hours of fermentation.

Accordingly, the at least one lactic acid bacteria strain of the present description is not compatible with the production of sourdough breads characterized by a pH after fermentation of between 3.3 and 4.

In one embodiment, the quick release of lactic acid from the at least one lactic acid bacteria strain during the short fermentation may decreases the pH of the preferment by at least 0.1 pH units more than the pH of the short fermentation of a preferment without the at least one lactic acid bacteria strain of the present description (with yeast only). Preferably, the pH during the fermentation of the preferment is decreased of at least 0.2, more preferably the pH during the fermentation of the short preferment is decreased of at least 0.3. It is understood that a lower pH improves the ability of gluten to swell and contributes to the texture, structure and leavening activity of the sponge.

Accordingly, the term "effective amount" when used herein will be understood to refer to the amount of the at least one lactic acid bacteria strain necessary to achieve a desired effect, such as a quick release of lactic acid during the short fermentation period to decrease the pH of the preferment.

Yeast may be added at any point in the method for making a dough mixture. In one embodiment, the first portion of dough ingredients in step a) comprises flour, water and yeast. In this embodiment, the first portion of dough ingredients comprises all of the yeast required for the process meaning that the remaining portion of dough ingredients does not comprise yeast. In other words, an effective amount of the at least one lactic acid bacteria strain of the present description may be mixed, with no particular order of addition, with flour, water and all of the yeast required to form the preferment. Breads or bread-like products made in accordance with this embodiment exhibit a more complex flavor than breads and bread-like products made using a short preferment method with yeast alone. However, the bread or bread-like products made in accordance with this embodiment maintain their characteristic alcoholic flavor. They also exhibit a crumb structure comparable with traditional processes with long fermentation times.

In another embodiment, the remaining portion of the dough ingredients comprises flour, water and yeast. In this embodiment, the remaining portion of dough ingredients comprises all of the yeast meaning that the first portion of dough ingredients does not comprise yeast. Because there is less yeast fermentation during the making of the dough mixture, breads or bread-like products made in accordance with this embodiment are less alcoholic. In other words, the at least one lactic acid bacteria strain of the present description may be mixed at step a) with flour and water while all of the yeast may be added at step c) with the remaining dough ingredients.

In a further embodiment, the first portion and the remaining portion of dough ingredients comprise flour, water and yeast. In this embodiment, the first portion of dough ingredients may comprise a first portion of yeast and the remaining portion of dough ingredient may comprise the remaining portion of yeast. It is understood that the amount of yeast may vary in the first portion and the remaining portion of dough ingredients depending on the recipe. Determination of the amount of yeast in the first portion and the remaining portion of dough ingredients is within the purview of those skilled in the art.

The lactic acid produced by the at least one lactic acid bacteria strain of the present description may remain in the bread or bread-like products after baking and increase their shelf-life by activating anti-molding organic acid based preservatives such as, for example, propionic acid, acetic acid, fumaric acid and the like, or may prevent or allow a reduction in the use of these anti-molding preservatives. Breads or bread-like products made in accordance with the last two embodiments exhibit a more complex and less alcoholic flavor than breads and bread-like products made using a short preferment method with yeast alone. Also, breads or bread-like products made in accordance with the last two embodiments have flavors similar to breads or bread-like products made according to traditional processes. Also, breads made in accordance with the last two embodiments exhibit a crumb structure comparable with traditional processes with long fermentation times.

It is understood that the remaining portion of dough ingredients may also comprise any other suitable ingredients for the purpose of making a dough mixture. Non-limiting examples of other suitable ingredients includes anti-molding organic acid based preservatives, oils, salt, sweeteners, emulsifiers, other flavorings and the like.

In an embodiment, the yeast may be a yeast from the genus *Saccharomyces* or any non-*Saccharomyces* yeast. The non-*Saccharomyces* yeast is selected from the group consisting of *Candida* sp, *Hanseniaspora* sp, *Hansenula* sp, *Kluyveromyces* sp, *Metschnikowia* sp, *Pichia* sp, *Starmerella* sp and *Torulaspora* sp. Preferably, the yeast is *Saccharomyces cerevisae* or *Cyberlindnera jadinii* (Torula yeast).

In an embodiment, the at least one lactic acid bacteria strain is from the genera *Lactobacillus, Lactococcus, Streptococcus, Leuconostoc* or *Pediococcus*. Preferably, the at least one lactic acid bacteria strain is a *Lactococcus lactis* strain. More preferably it is a biologically pure culture of *Lactococcus lactis* strain 82207 having accession number IDAC 270613-01 filed on Jun. 27, 2013.

As mentioned above, an effective amount of the at least one lactic bacteria strain may be necessary to achieve a quick release of lactic acid during the fermentation of the preferment. In an embodiment, the at least one lactic acid bacteria strain may have a number of colony forming units (CFU) per gram of flour in the preferment of at least $1e^7$ CFU/g of flour, preferably at least $5e^7$ CFU/g of flour in the preferment, and more preferably at least $1e^8$ CFU/g of flour in the preferment and most preferably at least $2e^8$ CFU/g of flour in the preferment.

In an embodiment, the yeast may be at a concentration of between 2 and 4% per g of total flour. Preferably at a concentration of 3% per g of total flour. It is understood that the term "total flour" means all of the flour required for making the dough mixture of the present description. Similarly, the yeast means all of the yeast required for making the dough mixture of the present description.

The preferment of the present description may be fermented between 1 and 5 hours. Preferably, the preferment may be fermented between 2 and 4 hours. Fermentation may be performed between room temperature and 35° C., preferably about 30° C. The rate of hydration of the preferment during fermentation may be at least 50%, at least 60%, at least 70%, at least 80%, at least 90% or 100%.

As mentioned above, the first portion of dough ingredients may comprise other ingredients such as, for example, sugar. Non-limiting examples of sugar include sucrose, fructose, glucose, lactose and mixtures thereof. In an embodiment, sucrose may be used at a concentration of at least 0.5% (g sugar / g of flour of preferment), at least 1% or at least 2%. In another embodiment, fructose may be used at a concentration of at least 4% (g/g). In another embodiment, glucose or lactose may be used at a concentration of at least 1% or at least 2% (g/g).

With the expansion of freezing-distribution mechanisms, the commercial marketing of frozen dough for home baking or on-premise baking in supermarkets continues to grow in volume. Therefore, the method for making a dough mixture in accordance with the present description further comprising the steps of cooling or freezing the fermented preferment obtained from step b) for a period up to 48 hours and warming the cooled or frozen fermented preferment before mixing with the remaining portion of the dough ingredients to form the dough mixture.

In one embodiment of the invention, the at least one lactic acid bacteria strain of the present disclosure may be prepared in freeze-dried form. The at least one lactic acid bacteria strain may be cultivated in an optimized and controlled culture media. It is understood that the cultivation and the culture media conditions are within the purview of the skilled person in the art. The resulting fermented broth may be centrifuged to produce a concentrated lactic acid bacteria cream which may be further mixed with a cryo-protecting formula before being lyophilized.

In another embodiment, the at least one lactic acid bacteria strain may be in a liquid-frozen form. The at least one lactic acid bacteria strain may be cultivated in an optimized and controlled culture media similar to the previous embodiment. The fermented broth may be centrifuged to produce a concentrated lactic acid bacteria cream which may be further mixed with a cryo-protecting formula and deep frozen. The liquid-frozen lactic acid bacteria composition may be potentially less expensive than the freeze-dried alternative and may possibly result in better production yields due to reduced bacterial loss during the freeze-drying process.

The dough mixture obtained in accordance with the present disclosure may be used for the manufacture of leavened goods such as, for example bread and bread-like products. Non-limiting examples of bread-like products include rolls, bagels, wheat flour tortillas, pizza crusts, donuts, croissants and pita breads.

Various modifications and variations will be apparent to those skilled in the art without departing from the scope and spirit of the present invention. Although the present invention has been described in connection with specific embodiments, it should be understood that the invention as claimed should not be unduly limited to such specific embodiments. Indeed, various modifications of the invention which are obvious to those skilled in fermentation, dough and bread production, bacterial cultures and related fields are intended to be within the scope of the following claims.

Therefore, the scope should be determined by the appended claims and their legal equivalents, and not by the examples given.

EXAMPLES

Example 1:

Comparison of Different Lactic Acid Bacteria Strains with Different Lag Phases for Acidification of a Pre-ferment The pH of the dough mixture during and after the pre-ferment was evaluated using three different lactic acid bacteria strains: the lactic acid bacteria strain R2207 having accession number IDAC 270613-01 filed on Jun. 27, 2013 and two other lactic acid bacteria strains EQ-01 and EQ-12. This test was performed over 16 hours as lactic acid bacteria present in the preferment may exhibit bacterial activity after the completion of fermentation of the preferment during the proofing of the dough mixture (acid tolerant lactic acid bacteria), thereby affecting the flavor and structure of breads or bread-like products produced therefrom.

Figure 2:
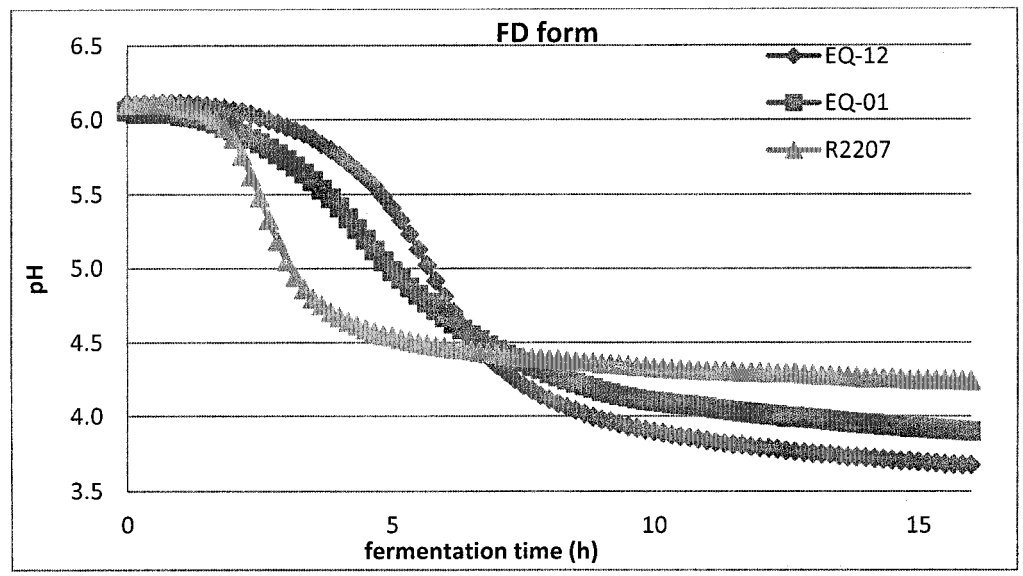
FIG. 2 illustrates the acidification activity of different lactic acid bacteria strains in freeze-dried form, showing the different lag phases characteristic from each strain in accordance with another embodiment of the invention.

The strains R2207 having accession numbers IDAC 270613-01, EQ-01 and EQ0-12 were independently mixed with flour and water to form 3 different preferments. Hydration was 100% (on flour weight) and the bacteria strain concentration was $2e^8$ CFU/g of flour for the three preferments. Flour used was a wheat flour T80 (ash content between 0.7 and 0.8%) and fermentation was performed at 30° C. The three preferments were fermented for up to 16 hours. As shown in FIGS. 1 and 2, the lactic acid bacteria strain R2207 having accession number IDAC 270613-01 exhibited a shorter lag phase i.e. a quick release of lactic acid was observed between 2 and 4 hours of fermentation. Accordingly, the pH during the fermentation was rapidly decreased in response to the release of lactic acid when compared to EQ-01 and EQ-12 strains. As shown by the pH of the dough mixture after 16 hours of 4.25, the strain R2207 having accession number IDAC 270613-01 has a low pH tolerance. In comparison, both fermentations with EQ-01 and EQ-12 strains exhibit a pH below 4 after 16 hours. The results from FIGS. 1 and 2 suggest that the performance of the lactic acid bacteria strain R2207 having accession number IDAC 270613-01 was the same whether it was freeze-dried or in liquid-frozen form.

These results indicate that the strain R2207 having accession number IDAC 270613-01 has a short lag phase consistent with bacterial activity during a short preferment. Also, the limited acid tolerance of the strain R2207 having accession number IDAC 270613-01 demonstrates it is not compatible with the production of sourdough breads with a pH between 3.3 and 4.

The lactic acid bacteria strains EQ-01 and EQ-12 exhibited longer lag phases independently of their form (freeze-dried of in liquid-frozen form) compared to the lactic acid bacteria strain R2207 having accession number IDAC 270613-01. It is of note that The EQ-12 showed a shorter lag phase in liquid-frozen form than in freeze-dried form.

Moreover, FIGS. 1 and 2 suggest that the EQ-01 and EQ-12 strains are acid-tolerant lactic acid bacteria strains because they were still producing lactic acid after 15 hours. Consequently, the pH after 15 hours fermentation was below 4 and was still decreasing in response to the continuous release of lactic acid. The pH of the strain R2207 having accession number IDAC 270613-01 was stabilized in a shorter fermentation time, which demonstrates its limited acid tolerance.

Example 2:

Bake Test with Short-preferment method Using *Lactococcus lactis* Strain R2207 having Accession Number IDAC 270613-01

Preferments or sponges were prepared by mixing Heritage flour at 57% humidity, water pre-warmed at 30° C. and *Lactococcus lactis* strain R2207 having accession number IDAC 270613-01 in freeze dried forms. Four bacterial concentrations were tested: $1.2e^7$ (sponge 1), $4e^7$ (sponge 2), $1.2e^8$ (sponge 3) and $4e^8$ CFU/g of flour (sponge 4). One negative control and one control with yeast were prepared. Fermentation was performed for 3 hours at 30° C. At the dough step, the sponge was combined with flour, water, canola oil 3%/total flour, HCFS 12%/total flour, yeast, salt 2.25%/total flour, fermaid XTR 1.5%/total flour and calpro 0.25%/total flour. The ratio of preferemted flour to total flour was 50%. The ratio of baker's yeast to total flour was 3% for the samples, 3.4% for the two controls. The dough temperature target was 26.6° C. Proofing was performed at 44° C. and 88% R.H. to 10 cm height. Dough was then baked in national oven at 227° C. for 17 minutes.

Bacteria sponge 1 exhibited a plain flavor comparable to the uninoculated sponge. Sponge 2 exhibited a slightly sour and pleasant flavor, while sponge 3 was sour and still pleasant. Sponge 4 exhibited a strong and very sour flavour. All sponges inoculated with the *Lactococcus lactis* strain R2207 having accession number IDAC 270613-01 can easily be differentiated from the yeast sponge that was very yeasty. Breads made from the inoculated sponges had flavours similar to breads produced with traditional methods and long proofing times.

Example 3

The following fermentation procedures were made in order to show that the pre-fermented sponge made in accordance with the present description can produce breads having structure and flavor characteristics comparable to traditional sourdough:

| PREFERMENTS | 1 | 2 |
|---|---|---|
| Flour 55 Special | 1000 | 1000 |
| Water 30° C. | 570 | 570 |
| Block yeast | 0 | 0 |
| L62 | 1 | 0 |
| strain R2207 having accession number IDAC 270613-01 | | 1 |
| Total weight | 1571 | 1571 |
| Fermentation time | 20 h | 3 h |
| Fermentation temperature | 30° C. | 30° C. |
| | 0.1% L62 | 0.1% R2207 |

Strain R2207 having accession number IDAC 270613-01 is a quickly acidifying strain of *Lactococcus lactis* with limited acid tolerance. L62 strain is an acid tolerant *Lactobacillus brevis* used for the production of sourdough breads.

Figure 3:
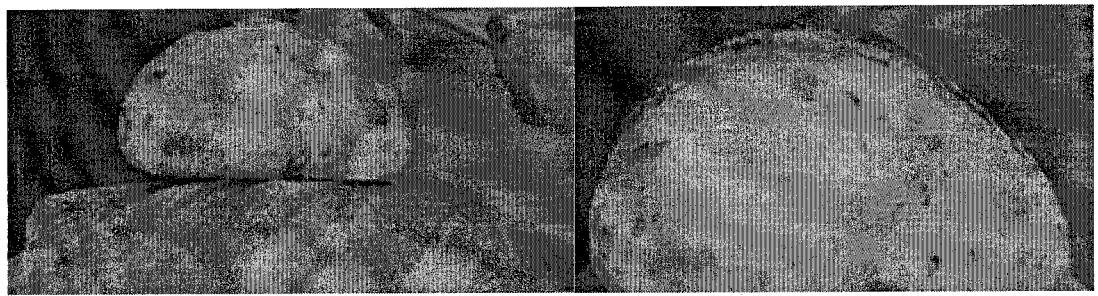
FIG. 3 illustrates the crumb structure of breads produced with *Lactobacillus brevis*, strain L62 (acid tolerant strain used in the production of sourdough breads) and with *Lactococcus lactis*, strain R2207 having accession number IDAC 270613-01 filed on Jun. 27, 2013 (quickly-acidifying strain with limited acid tolerance). The crumb structure of breads produced with a short preferment of three hours is comparable to breads produced with a traditional method and a fermentation time of 20 hours.
Figure 3:
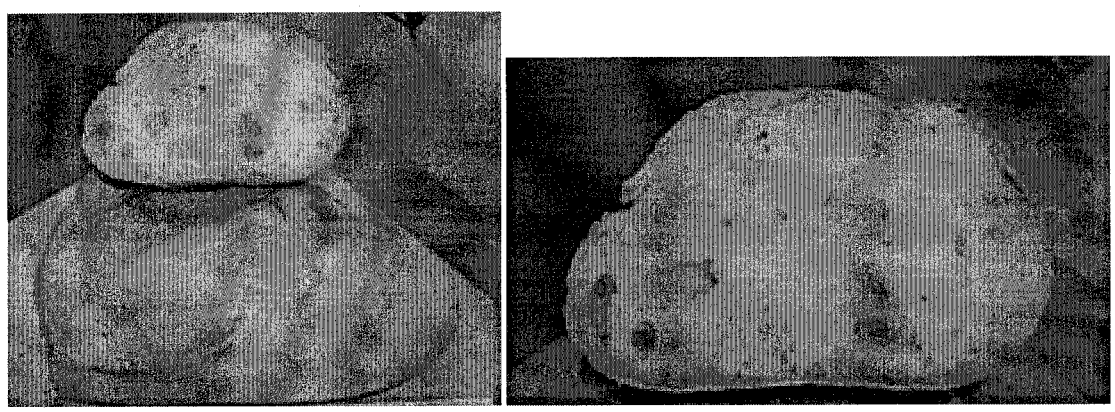

At the dough step, the pre-ferment was combined with flour, water, yeast, salt 2%/total flour, bread improver 0.5%/total flour. The ratio of pre-fermented flour to total flour was 50% for both cases. The ratio of baker's yeast to total flour was 2% for both cases. Hydration rate was 55.5%/total flour. A Hobart mixer was used for 1 minute at low speed and 8 minutes at high speed until full dough development. The doughs were bulk proofed for 15 minutes and then divided into 400g pieces and rounded by hand. Bench time was 10 minutes, after what the pieces were molded. A final proofing of 60 minutes at 30° C., 80% R.H, and then the doughs were baked for 25 minutes at 225° C. in a hearth oven. Pictures of the breads are shown in FIG. 3.

The L62 sponge was liquid after 20h, while mixing this negatively influenced the dough development, showing stickiness, more elastic and with quick development, but dough was also slack. During bench proofing the dough improved in quality and had good oven spring. It resulted in a pleasant taste and good crumb structure.

With R2207 sponge, while mixing the sponge had good appearance, the dough was very good in terms of handling. Doughs showed good performances, good oven spring and final taste was better than with L62 sponge's breads.

The quickly acidifying strain R2207 is not adapted to traditional sourdough process, but gave good results in terms of aroma profile and crumb structure when used in a short preferment in accordance with the present description. Accordingly, the short preferment (3 hours) method with strain R2207 gave breads having a traditional flavor and a crumb structure comparable to traditional breads produced with a fermentation time of 20 hours.

While the invention has been described in connection with specific embodiments thereof, it will be understood that it is capable of further modifications and this description is intended to cover any variations, uses, or adaptations of the invention following, in general, the principles of the invention and including such departures from the present disclosure that come within known or customary practice within the art to which the invention pertains and as may be applied to the essential features hereinbefore set forth, and as follows in the scope of the appended claims.

What is claimed is:

1. A method for making a dough mixture, the method comprising the steps of a) mixing an effective amount of at least one limited acid tolerant *lactococcus lactis* strain with a first portion of dough ingredients to form a preferment;
b) allowing the preferment to ferment for 1 to 5 hours; and
c) mixing the fermented preferment with a remaining portion of the dough ingredients to form the dough mixture;

wherein the at least one limited acid tolerant *lactococcus lactis* strain releases lactic acid during the first 4 hours of the fermentation of the preferment until the pH becomes inhibitory to the growth of the at least one *lactococcus lactis* strain.

2. The method of claim 1 wherein the release of the lactic acid decreases the pH during the fermentation by at least 0.1 pH units more than fermentation without the at least one limited acid tolerant *lactococcus lactis* strain.

3. The method of claim 1, wherein the first portion dough ingredients comprises flour, water and yeast.

4. The method of claim 1, where the remaining portion of dough ingredients comprises flour, water and yeast.

5. The method of claim 1, wherein the first portion and the remaining portion of dough ingredients comprise flour, water and yeast.

6. The method of claim 1 further comprising freezing the fermented preferment obtained from step b) for a period up to 48 hours and warming the frozen fermented preferment before mixing with the remaining portion of dough ingredients to form the dough mixture.

7. The method of claim 4 wherein the yeast is from the genus *Saccharomyces* or non-*Saccharomyces* yeast.

8. The method of claim 7, wherein the non-*Saccharomyces* yeast is selected from the group consisting of *Candida* sp, *Hanseniaspora* sp, *Hansenula* sp, *Kluyveromyces* sp, *Metschnikowia* sp, *Pichia* sp, *Starmerella* sp, and *Torulaspora* sp, and wherein preferably, the yeast is *Saccharomyces cerevisae* or *Cyberlindnera jadinii* (Torula yeast).

9. The method of claim 1, wherein the at least one limited acid tolerant *lactococcus lactis* strain is a biologically pure culture of *Lactococcus lactis*, strain R2207 having accession number IDAC 270613-01 filed on Jun. 27, 2013.

10. The method of claim 1, wherein the at least one limited acid tolerant *lactococcus lactis* strain has a number of colony forming units (CFU) per gram of flour of at least $1e^7$ CFU/g of flour.

11. The method of claim 1, wherein the yeast is at a concentration of between 2 and 4% per gram weight of flour.

* * * * *